United States Patent
Jain

(10) Patent No.: US 11,969,420 B2
(45) Date of Patent: Apr. 30, 2024

(54) COMBINATION THERAPY OF CRENOLANIB AND APOPTOSIS PATHWAY AGENTS FOR THE TREATMENT OF PROLIFERATIVE DISORDERS

(71) Applicant: Arog Pharmaceuticals, Inc., Plano, TX (US)

(72) Inventor: Vinay K. Jain, Dallas, TX (US)

(73) Assignee: AROG PHARMACEUTICALS, INC., Plano, TX (US)

(*) Notice: Subject to any disclaimer, the term of this patent is extended or adjusted under 35 U.S.C. 154(b) by 82 days.

(21) Appl. No.: 17/320,455

(22) Filed: May 14, 2021

(65) Prior Publication Data

US 2022/0133710 A1    May 5, 2022

Related U.S. Application Data

(60) Provisional application No. 63/107,969, filed on Oct. 30, 2020.

(51) Int. Cl.
  *A61K 31/4709* (2006.01)
  *A61K 31/706* (2006.01)
  *A61K 45/06* (2006.01)

(52) U.S. Cl.
  CPC ........ *A61K 31/4709* (2013.01); *A61K 31/706* (2013.01); *A61K 45/06* (2013.01)

(58) Field of Classification Search
  CPC .. A61K 31/4709; A61K 31/706; A61K 45/06; A61K 2300/00
  See application file for complete search history.

(56) References Cited

U.S. PATENT DOCUMENTS

| | | |
|---|---|---|
| 5,990,146 A | 11/1999 | Boschelli et al. |
| 7,183,414 B2 | 2/2007 | Tom et al. |
| 9,023,880 B2 | 5/2015 | Jain |
| 9,101,624 B2 | 8/2015 | Jain |
| 9,393,240 B2 | 7/2016 | Jain |
| 9,480,683 B2 | 11/2016 | Jain |
| 9,801,869 B2 | 10/2017 | Jain |
| 9,801,870 B2 | 10/2017 | Jain |
| 9,889,127 B2 | 2/2018 | Jain |
| 10,213,423 B2 | 2/2019 | Jain |
| 10,251,877 B2 | 4/2019 | Jain |
| 10,463,658 B2 | 11/2019 | Jain |
| 10,780,086 B2 | 9/2020 | Jain |
| 2004/0049032 A1 | 3/2004 | Charrier et al. |
| 2005/0124599 A1 | 6/2005 | Kath et al. |
| 2019/0091229 A1 | 3/2019 | Lichenstein et al. |
| 2019/0183880 A1 | 6/2019 | Jain |
| 2020/0147117 A1 | 5/2020 | Ben Yakar et al. |
| 2023/0053688 A1* | 2/2023 | Roth .......... A61P 35/00 |

FOREIGN PATENT DOCUMENTS

| | | |
|---|---|---|
| WO | 1999016755 A1 | 4/1999 |
| WO | 2001040217 A1 | 6/2001 |
| WO | 2002032861 A2 | 4/2002 |
| WO | 2003024931 | 3/2003 |
| WO | 2003024969 | 3/2003 |
| WO | 2003035009 | 5/2003 |
| WO | 2003037347 | 5/2003 |
| WO | 2003057690 | 7/2003 |
| WO | 2004005281 A1 | 1/2004 |
| WO | 2004016597 A2 | 2/2004 |
| WO | 2004018419 A2 | 3/2004 |
| WO | 2004039782 A1 | 5/2004 |
| WO | 2004046120 A2 | 6/2004 |
| WO | 2004058749 A1 | 7/2004 |

OTHER PUBLICATIONS

Adams, et al. "The BCL-2 arbiters of apoptosis and their growing role as cancer targets" Cell Death and Differentiation (2018) 25, 27-36.

Aikawa, et al. "Quizartinib, a selective FLT3 inhibitor, maintains antileukemic activity in preclinical models of RAS-mediated midostaurinresistant acute myeloid leukemia cells" Oncotarget, 2020, vol. 11, (No. 11), pp. 943-955.

Amin, et al. "Having a higher blast percentage in circulation than bone marrow: clinical implications in myelodysplastic syndrome and acute lymphoid and myeloid leukemias" Leukemia (2005) 19, 1567-1572, published online Jul. 28, 2005.

Chua, et al. "Chemotherapy and Venetoclax in Elderly Acute Myeloid Leukemia Trial (CAVEAT): A Phase lb Dose-Escalation Study of Venetoclax Combined With Modified Intensive Chemotherapy" Journal of Clinical Oncology, Jul. 2020.

Chyla, et al. "Genetic biomarkers of sensitivity and resistance to venetoclax monotherapy in patients with relapsed acute myeloid leukemia" Am J Hematol. May 17, 2018;93(8):E202-E205. doi: 10.1002/ajh.25146.

DiNardo, et al. Mutant IDH (mIDH) inhibitors, ivosidenib or enasidenib, with azacitidine (AZA) in patients with acute myeloid leukemia (AML). May 2018, Journal of Clinical Oncology 36 (15_suppl):7042-7042, Abstract Only.

DiNardo, et al. "Molecular patterns of response and treatment failure after frontline venetoclax combinations in older patients with AML 2020" Blood, Mar. 12, 2020 | vol. 135, No. 11.

Dombret, et al. "International phase 3 study of azacitidine vs conventional care regimens in older patients with newly diagnosed AML with >30% blasts" Blood, Jul. 16, 2015 x vol. 126, No. 3.

Frenzel, et al. "Bcl2 family proteins in carcinogenesis and the treatment of cancer" Apoptosis. Apr. 2009 ; 14(4): 584-596. doi:10. 1007/s10495-008-0300-Z.

(Continued)

*Primary Examiner* — Sun Jae Yoo
(74) *Attorney, Agent, or Firm* — Edwin S. Flores; Daniel J. Chalker; Chalker Flores, LLP

(57) ABSTRACT

The present invention includes methods for treating a proliferative disorder comprising administering a therapeutically effective amount of crenolanib or a salt thereof in combination with pharmaceutical agent targeting apoptosis pathway proteins wherein the crenolanib and other agent are provided at least one of sequentially or concomitantly in a subject for use in the treatment of the proliferative disease, wherein the subject is a human subject.

13 Claims, No Drawings

(56) References Cited

OTHER PUBLICATIONS

Garz, et al. "Azacitidine combined with the selective FLT3 kinase inhibitor crenolanib disrupts stromal protection and inhibits expansion of residual leukemia-initiating cells in FLT3-ITD AML with concurrent epigenetic mutations" Oncotarget, 2017, vol. 8, (No. 65), pp. 108738-108759.
GenBank (accession No. NM_04119.2), PRI Aug. 4, 2019.
GenPept (accession No. NP_004110.2), PRI Jul. 11, 2021.
Goldberg, Aaron "Crenolanib Combined with Chemotherapy in FLT3 AML" 2020, Power point presentation for 4th Annual Think Tank on Integrating New Molecular Targets in Acute Leukemias and Myeloproliferative Neoplasms.
Griswold, et al. "Effects of MLN518, a dual FLT3 and KIT inhibitor, on normal and malignant hematopoiesis" Blood, Nov. 1, 2004, vol. 104, No. 9.
Joerger, et al. "The p53 Pathway: Origins, Inactivation in Cancer, and Emerging Therapeutic Approaches" Annu. Rev. Biochem. 2016. 85:375-404, First published online as a Review in Advance on May 4, 2016.
Konopleva, et al. "MDM2 inhibition: an important step forward in cancer therapy" published online Jul. 10, 2020, Springer Nature.
Konopleva, et al. "Efficacy and Biological Correlates of Response in a Phase II Study of Venetoclax Monotherapy in Patients with Acute Myelogenous Leukemia" Oct. 2016 Cancer Discovery, Published Online First Aug. 12, 2016; DOI: 10.1158/2159-8290.CD-16-0313.
Levis, et al. "Small Molecule FLT3 Tyrosine Kinase Inhibitors" Current Pharmaceutical Design, 2004, 10, 1183-1193.
Levis, et al. "AFLT3-targeted tyrosine kinase inhibitor is cytotoxic to leukemia cells in vitro and in vivo" Blood, Jun. 1, 2002 vol. 99, No. 11.
Lewis, et al. "Phase I Study of the Safety, Tolerability, and Pharmacokinetics of Oral CP-868,596, a Highly Specific Platelet-Derived Growth Factor Receptor Tyrosine Kinase Inhibitor in Patients With Advanced Cancers" Journal of Clinical Oncology, vol. 27, No. 31, Nov. 1, 2009.
Medeiros, et al. "A Phase I/II Trial of the Combination Azacitidine and Gemtuzumab Ozogamicin for Treatment of Relapsed Acute Myeloid Leukemia" Clinical Lymphoma, Myeloma and Leukemia, 2018, DOI: 10.1016/j.clml.2018.02.017.
Merino, et al. "BH3-Mimetic Drugs: Blazing the Trail for New Cancer Medicines" Cancer Cell 34, Dec. 10, 2018.
Murata, et al. "Selective Cytotoxic Mechanism of GTP-14564, a Novel Tyrosine Kinase Inhibitor in Leukemia Cells Expressing a Constitutively Active Fms-like Tyrosine Kinase 3 (FLT3)" The Journal of Biological Chemistry vol. 278, No. 35, Issue of Aug. 29, pp. 32892-32898, 2003, vol. 278, No. 35, Issue of Aug. 29, pp. 32892-32898, 2003.
O'Farrell, et al. "SU11248 is a novel FLT3 tyrosine kinase inhibitor with potent activity in vitro and in vivo" Blood, May 1, 2003, vol. 101, No. 9.
Small, Donald "FLT3 Mutations: Biology and Treatment" American Society of Hematology, 2006, 178-184.
Smith, et al. "Single-agent CEP-701, a novel FLT3 inhibitor, shows biologic and clinical activity in patients with relapsed or refractory acute myeloid leukemia" Blood, May 15, 2004, vol. 103, No. 10.
Stone, et al. "Patients with acute myeloid leukemia and an activating mutation in FLT3 respond to a small-molecule FLT3 tyrosine kinase inhibitor, PKC412" Blood, Jan. 1, 2005 vol. 105, No. 1.
UniProt (accession No. P36888-1) (FLT3_HUMAN), Receptor-type tyrosine-protein kinase FLT3, Last modified: Jun. 2, 2021.
Von Mehren, et al. "Dose escalating study of crenolanib besylate in advanced GIST patients with PDGFRA D842V activating mutations" 2016.
Yee, et al. "SU5416 and SU5614 inhibit kinase activity of wild-type and mutant FLT3 receptor tyrosine kinase" Blood, Oct. 15, 2002 vol. 100, No. 8, 2941-2949.
Yoshimoto, et al. "FLT3-ITD up-regulates MCL-1 to promote survival of stem cells in acute myeloid leukemia via FLT3-ITD-specific STAT5 activation" Blood, Dec. 3, 2009 vol. 114, No. 24, 5034-5043.
Zhang, et al. "APR-246 reactivates mutant p53 by targeting cysteines 124 and 277" Zhang et al. Cell Death and Disease (2018) 9:439.
Aboudalle, et al. "Phase 1-11 Study of Crenolanib Combined with Standard Salvage Chemotherapy and Crenolanib Combined with 5-Azacitidine in Acute Myeloid Leukemia Patients with FL T3 Activating Mutations" Blood (20018) 132 (Supplement 1): 2715.
Kayser, et al. "Advances in Targeted Therapy for Acute Myeloid Leukaemia" Br J Haematol. Feb. 2018; 180(4): 484-500. doi:JO.lllllbjh.15032.
Myshko, Denise "Eprenetapopt May Develop Into New Option for TP53-Mutant MDS" Oct. 7, 2020, OncologyLive, \A:ll. 21/No. 19, \A:llume 21, Issue 19.
United States Patent & Trademark Office (ISA), International Search Report and Written Opinion for PCT/US2021/032719 dated Sep. 1, 2021, 11 pp.

\* cited by examiner

COMBINATION THERAPY OF CRENOLANIB AND APOPTOSIS PATHWAY AGENTS FOR THE TREATMENT OF PROLIFERATIVE DISORDERS

CROSS-REFERENCE TO RELATED APPLICATIONS

This application claims priority to U.S. Provisional Application Ser. No. 63/107,969, filed Oct. 30, 2020, the entire contents of which are incorporated herein by reference.

TECHNICAL FIELD OF THE INVENTION

This invention pertains to crenolanib, or salts thereof, and other pharmaceutical agents for the treatment of proliferative disorders, and to a method of treatment of warm-blooded animals, preferably humans, in which a therapeutically effective dose of crenolanib and another pharmaceutical agent is administered to a subject suffering from said disease or condition.

STATEMENT OF FEDERALLY FUNDED RESEARCH

Not applicable.

INCORPORATION-BY-REFERENCE OF MATERIALS FILED ON COMPACT DISK

Not applicable.

BACKGROUND OF THE INVENTION

Without limiting the scope of the invention, its background is described in connection with cancer treatments and the use of novel combination therapies that include crenolanib.

One of the hallmarks of cancer cells is resistance to apoptosis, or programmed cell death. In normal tissues, a balance is maintained between pro-survival and pro-apoptotic factors. When partially activated, the pro-apoptotic BAX/BAK-like proteins are bound and inhibited by the pro-survival BCL-2 family proteins (BCL-2, BCL-XL, BCL-W, and MCL-1) (Adams and Cory 2018). This interaction prevents the full activation of BAX/BAK, which necessitates oligomerization before these proteins can induce mitochondrial outer membrane permeabilization, a key step in apoptosis. Under stress, apoptosis is induced when BH3-only proteins bind to and inhibit BCL-2 family members which frees BAX/BAK to oligomerize and apoptosis to proceed (Adams and Cory 2018).

One of the various stressors that can induce apoptosis is the activation of p53, the "guardian of the genome". In a healthy cell, DNA damage, oxidative stress, or other stressors induce p53 activation. In turn, p53 activates various pathways, including the pro-apoptotic BAX. Activation of p53 is heavily regulated, in part by the inhibitor Mouse double minute 2 homolog (MDM2, also known as E3 ubiquitin-protein ligase Mdm2, OMIM: 164785 MGI: 96952 HomoloGene: 1793 GeneCards: MDM2, human MDM1 is Entrez: 4193, Uniprot: Q00987). Under normal conditions, MDM2 binds to and inhibits p53, and the release of p53 by MDM2 is part of the apoptotic process (Joerger and Fersht 2016).

Due to the highly interactive and regulated nature of apoptosis, there are multiple places where mutations or dysregulation can lead to apoptosis resistance in cancer cells. For instance, inactivating mutations in p53 are the most common mutation across all cancer types. Full or partial chromosomal loss of p53 (located on chromosome 17p) are also found in various cancers, including acute myeloid leukemia (Joerger and Fersht 2016). In addition to p53 inactivation, high levels of MDM2 or BCL-2 family member expression is common in many cancers. This disruption of the normal balance in pro-survival to pro-apoptotic proteins, i.e., a higher level of pro-survival proteins relative to pro-apoptotic proteins, leads to apoptosis resistance (Frenzel, Grespi et al. 2009). This pro-survival state contributes to both cancer cell survival in the face of environmental stressors such as anoikis and hypoxia and to resistance to chemotherapeutic agents, which often depend on the induction of apoptosis for their mechanism of action.

In light of the central role of the pro-survival BCL-2 proteins and p53 regulators such as MDM2 in tumorigenesis and chemoresistance, the development of drugs targeting these pathways, or even drugs designed to stabilize p53, is an attractive prospect for the treatment of various cancers. Several drugs targeting members of the apoptosis pathway have been testing in clinical trials across a number of cancers. Non-limiting examples of these include the BCL-2 specific inhibitor venetoclax, the BCL-2/BCL-XL inhibitor navitoclax, the MCL-1 inhibitor AMG-397, the MDM2 inhibitor idasnutlin, and the p53 stabilizer/activator eprenetapopt (Merino, Kelly et al. 2018, Zhang, Bykov et al. 2018, Konopleva, Martinelli et al. 2020). However, to date these drugs have shown limited activity as monotherapy in most cancers, possibly due to both the redundancy of BCL-2 protein family members and the fact that BCL-2 protein inhibition may "prime" a cell for apoptosis. Thus, a second signalling pathway is necessary to fully push the cell into programmed cell death. Therefore, combination approaches using chemotherapeutic agents, hypomethylating agents, proteosome inhibitors, kinase inhibitors, and monoclonal antibodies are being pursued (Merino, Kelly et al. 2018, Konopleva, Martinelli et al. 2020).

Venetoclax, a BCL-2 specific inhibitor, is the most thoroughly studied of these compounds. Venetoclax has received regulatory approval as a single agent in chronic lymphocytic leukemia and small lymphocytic leukemia. Venetoclax is also used in combination with azacitidine, decitabine, or low-dose cytarabine in older or unfit acute myeloid leukemia (AML) patients. While response rates in this historically poor-performing population were promising, a number of mechanisms of resistance have been identified, including FLT3.

As such, novel treatment regimens containing crenolanib, a FLT3 inhibitor, can fill the unmet need presented by FLT3 (also known as Cluster of differentiation antigen 135 (CD135), fms like tyrosine kinase 3 (FLT-3), receptor-type tyrosine-protein kinase FLT3, or fetal liver kinase-2 (Flk2)) mediated resistance to venetoclax and other pharmaceutical agents targeting apoptotic pathways.

SUMMARY OF THE INVENTION

In one embodiment, the present invention includes a method for treating a proliferative disorder comprising administering to a subject a therapeutically effective amount of crenolanib or a pharmaceutically acceptable salt thereof in combination with a BCL family protein inhibitor. In one aspect, the B-cell lymphoma (BCL) family protein inhibitor reduces the activity of at least one of B-cell lymphoma 2 (BCL-2), B-cell lymphoma-extra large (BCL-XL), Bcl-2- like protein 2 (BCL-W), and Induced myeloid leukemia cell differentiation protein Mcl-1 (MCL-1). In another aspect, the BCL family protein inhibitor is at least one of a BH3 mimetic, small molecule inhibitor, liposomal antisense molecule, or gene silencing peptide. In another aspect, the BCL protein inhibitor is selected from at least one of venetoclax, navitoclax, palcitoclax, APG-2575, AT101, AZD0466, AZD4320, BCL201, BP1002, MIK665, 563845, VAL 101, AMG-176, AZD5991, FL118, AMG-397, ABBV-467 or ABT-737. In another aspect, the invention further comprises providing the subject a chemotherapeutic agent that comprises one or more of hypomethylating agents, alkylating agents, antimetabolites, natural products, or a combination thereof. In another aspect, the hypomethylating agent is selected from azacitidine or decitabine. In another aspect, the chemotherapeutic agent is cytarabine. In another aspect, the proliferative disorder is characterized by a constitutively active mutated fms like tyrosine kinase 3 (FLT-3). In another aspect, the mutated FLT3 is selected from at least one of FLT3-ITD, FLT3-TKD, or FLT3-variants. In another aspect, the proliferative disorder is selected from at least one of a leukemia, myeloma, myeloproliferative disease, myelodysplastic syndrome, idiopathic idiopathic hypereosinophilic syndrome, bladder cancer, breast cancer, cervical cancer, central nervous system cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the subject has a newly diagnosed proliferative disorder, or has progressed on at least one prior line of therapy, or is in need of therapy to maintain remission. In another aspect, the crenolanib or pharmaceutically acceptable salt thereof is administered one of sequentially or concomitantly with the BCL-2 family protein inhibitor and other pharmaceutical agent. In another aspect, the crenolanib or pharmaceutically acceptable salt thereof and the BCL-2 family protein inhibitor are administered at least one of continuously, intermittently, systemically or locally for as long as the subject is in need of treatment for the proliferative disorder. In another aspect, the therapeutically effective amount of crenolanib or the pharmaceutically acceptable salt thereof and the BCL-2 family protein inhibitor and other pharmaceutical agent are administered orally, intravenously, or intraperitoneally. In another aspect, the therapeutically effective amount of crenolanib or the pharmaceutically acceptable salt thereof is administered up to three times a day. In another aspect, the therapeutically effective amount of crenolanib or the pharmaceutically acceptable salt thereof is from about 50 to 500 mg per day, 100 to 450 mg per day, 200 to 400 mg per day, 300 to 500 mg per day, 350 to 500 mg per day, or 400 to 500 mg per day. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate.

In another embodiment, the present invention includes a method for treating a proliferative disorder comprising administering to a subject a therapeutically effective amount of crenolanib or pharmaceutically acceptable salt thereof in combination with a Mouse double minute 2 homolog (MDM2) protein inhibitor. In one aspect, the MDM2 protein inhibitor is selected from at least one of idasanutlin, milademetan, siremadlin, AMG-232, ALRN-6924, APG-115, HQP1351, APG-2575, APG-1252 BI-907828, KRT-232, or CGM097. In another aspect, the invention further comprises providing the subject a chemotherapeutic agent that comprises one or more of hypomethylating agents, alkylating agents, antimetabolites, natural products, or a combination thereof. In another aspect, the hypomethylating agent is selected from azacitidine or decitabine. In another aspect, the chemotherapeutic agent is cytarabine. In another aspect, the proliferative disorder is characterized by a constitutively active mutated FLT3. In another aspect, the mutated FLT3 is selected from at least one of FLT3-ITD, FLT3-TKD, or FLT3-variants. In another aspect, the proliferative disorder is selected from at least one of a leukemia, myeloma, myeloproliferative disease, myelodysplastic syndrome, idiopathic hypereosinophilic syndrome, bladder cancer, breast cancer, cervical cancer, central nervous system cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the subject has a newly diagnosed proliferative disorder, or has progressed on at least one prior line of therapy, or is in need of therapy to maintain remission. In another aspect, the crenolanib or pharmaceutically acceptable salt thereof is administered one of sequentially or concomitantly with the MDM2 inhibitor and other pharmaceutical agent. In another aspect, the crenolanib or pharmaceutically acceptable salt thereof and the MDM2 protein inhibitor are administered at least one of continuously, intermittently, systemically or locally for as long as the subject is in need of treatment for the proliferative disorder. In another aspect, the therapeutically effective amount of crenolanib or the pharmaceutically acceptable salt thereof and the MDM2 protein inhibitor and other pharmaceutical agent are administered orally, intravenously, or intraperitoneally. In another aspect, the therapeutically effective amount of crenolanib or the pharmaceutically acceptable salt thereof is administered up to three times a day. In another aspect, the therapeutically effective amount of crenolanib or the pharmaceutically acceptable salt thereof is from about 50 to 500 mg per day, 100 to 450 mg per day, 200 to 400 mg per day, 300 to 500 mg per day, 350 to 500 mg per day, or 400 to 500 mg per day. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate.

In another embodiment, the present invention includes a method for treating a proliferative disorder comprising administering to a subject a therapeutically effective amount of crenolanib or pharmaceutically acceptable salt thereof in combination with a p53 activator. In one aspect, the p53 activator is selected from at least one of eprenetapopt, APR-548, p-28, COTI-2, kevetrin, PC14586, or CV5461. In another aspect, the invention further comprises providing the subject a chemotherapeutic agent that comprises one or more of hypomethylating agents, alkylating agents, antimetabolites, natural products, or a combination thereof. In another aspect, the hypomethylating agent is selected from azacitidine or decitabine. In another aspect, the chemotherapeutic agent is cytarabine. In another aspect, the proliferative disorder is characterized by a constitutively active mutated FLT3. In another aspect, the mutated FLT3 is selected from at least one of FLT3-ITD, FLT3-TKD, or FLT3-variants. In another aspect, the proliferative disorder is selected from at least one of a leukemia, myeloma, myeloproliferative disease, myelodysplastic syndrome, idiopathic hypereosinophilic syndrome, bladder cancer, breast cancer, cervical cancer, central nervous system cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, wherein the subject has a newly diagnosed proliferative disorder, or has progressed on at least one prior line of therapy, or is in need of therapy to maintain remission. In another aspect, the crenolanib or pharmaceutically acceptable salt thereof is administered one of sequentially or concomitantly with the p53 activator and other pharmaceutical agent. In another aspect, wherein the crenolanib or pharmaceutically acceptable salt thereof and the p53 activator are administered at least one of continuously, intermittently, systemically or locally for as long as the subject is in need of treatment for the proliferative disorder. In another aspect, the therapeutically effective amount of crenolanib or the pharmaceutically acceptable salt thereof and the p53 activator and other pharmaceutical agent are administered orally, intravenously, or intraperitoneally. In another aspect, the therapeutically effective amount of crenolanib or the pharmaceutically acceptable salt thereof is administered up to three times a day. In another aspect, the therapeutically effective amount of crenolanib or the pharmaceutically acceptable salt thereof is from about 50 to 500 mg per day, 100 to 450 mg per day, 200 to 400 mg per day, 300 to 500 mg per day, 350 to 500 mg per day, or 400 to 500 mg per day. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate.

In another embodiment, the present invention includes a method for treating a proliferative disorder comprising administering to a subject a therapeutically effective amount of crenolanib or pharmaceutically acceptable salt thereof in combination with a hypomethylating agent or DNA methyltransferase inhibitor. In one aspect, the hypomethylating agent is azacitidine or decitabine. In another aspect, the proliferative disorder is characterized by a constitutively active mutated FLT3. In another aspect, the mutated FLT3 is selected from at least one of FLT3-ITD, FLT3-TKD, or FLT3-variants. In another aspect, the proliferative disorder is selected from at least one of a leukemia, myeloma, myeloproliferative disease, myelodysplastic syndrome, idiopathic hypereosinophilic syndrome, bladder cancer, breast cancer, cervical cancer, central nervous system cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the subject has a newly diagnosed proliferative disorder, or has progressed on at least one prior line of therapy or is in need of therapy to maintain remission. In another aspect, the crenolanib or pharmaceutically acceptable salt thereof is administered one of sequentially or concomitantly with the hypomethylating agent or DNA methyltransferase inhibitor. In another aspect, the crenolanib or pharmaceutically acceptable salt thereof and the hypomethylating agent or DNA methyltransferase inhibitor are administered at least one of continuously, intermittently, systemically or locally for as long as the subject is in need of treatment for the proliferative disorder. In another aspect, the therapeutically effective amount of crenolanib or the pharmaceutically acceptable salt thereof and the hypomethylating agent or DNA methyltransferase inhibitor and other pharmaceutical agent are administered orally, intravenously, or intraperitoneally. In another aspect, the therapeutically effective amount of crenolanib or the pharmaceutically acceptable salt thereof is administered up to three times a day. In another aspect, the therapeutically effective amount of crenolanib or the pharmaceutically acceptable salt thereof is from about 50 to 500 mg per day, 100 to 450 mg per day, 200 to 400 mg per day, 300 to 500 mg per day, 350 to 500 mg per day, or 400 to 500 mg per day. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate.

BRIEF DESCRIPTION OF THE DRAWINGS

None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

The present invention is directed to the administration of crenolanib, or a pharmaceutically acceptable salt thereof, to subjects suffering from a proliferative disease or proliferative disorder in order to treat the disease or disorder, and/or to prevent worsening of the disease or disorder.

In a study investigating patterns of response and relapse in 81 AML patients treated with venetoclax combination therapy, only 1 of 9 of patients with FLT3 mutations at baseline achieved a durable remission (remission lasting at least 12 months) on venetoclax combination therapy. Moreover, in patients who initially responded to venetoclax therapy but relapsed within 12 months, 16% showed expansion of the mutated FLT3 clone and an additional 8% acquired new FLT3 mutations at relapse (DiNardo, Tiong et al. 2020). Other studies investigating the efficacy of venetoclax single agent or combination regimens in AML have found similar results in FLT3 mutated patients (Konopleva, Pollyea et al. 2016, Chyla, Daver et al. 2018, Chua, Roberts et al. 2020). Therefore, not only is mutated FLT3 at baseline predictive of primary resistance, acquisition of FLT3 mutations or dysregulation of the FLT3 signalling pathway such as, by example, loss of function mutations in CBL or upregulation of the FLT3 ligand, after initial response to venetoclax cause adaptive resistance and relapse.

Detailed in vitro studies have elucidated a possible molecular mechanism underlying FLT3-mutation resistance to venetoclax. In cells expressing mutated FLT3, specifically the constitutively active FLT3-ITD mutation, the expression of MCL-1 and BCL-XL are increased compared to cells transfected with an empty vector (DiNardo, Tiong et al. 2020). It was found that FLT3-ITD mutated cells are less dependent on BCL-2 as a pro-survival signal and targeting BCL-2 specifically with venetoclax is not effective. Cell viability studies confirmed that these cells are resistant to venetoclax as a single agent and remain resistant to venetoclax-azacitidine or venetoclax-cytarabine combination. However, FLT3 mutant cells were sensitive to the FLT3 inhibitors midostaurin and gilteritinib. Furthermore, combining FLT3 inhibitors with venetoclax showed that treatment with FLT3 inhibitors sensitizes FLT3-mutated cells to venetoclax (DiNardo, Tiong et al. 2020). Preclinical in vivo studies using the FLT3 inhibitor quizartinib confirm these results (Chyla, Daver et al. 2018). Combining FLT3 inhibitors with the standard of care venetoclax-hypomethylating agent combination therapy sensitizes FLT3-mutated leukemia to treatment and may help prevent FLT3-mediated relapse in patients with FLT3-wildtype disease at baseline. However, it is not known if the effect of FLT3 inhibitors with venetoclax may work with other apoptotic pathway targeting agents.

FLT3 signaling, as a receptor tyrosine kinase, promotes cell survival. Activating mutations that lead to ligand independent activation promote aberrant cell survival, partly through an increase in expression of the pro-survival BCL family proteins MCL-1 and BCL-XL, as discussed above (Yoshimoto, Miyamoto et al. 2009, DiNardo, Tiong et al. 2020). Blocking FLT3 signaling through the use of small molecule inhibitors cuts off this pro-survival signal, while BCL or MDM2 inhibitors and/or p53 activators promote a pro-apoptotic profile. Treatment paradigms combining these classes of agents with FLT3 inhibitors, either as doublet therapy or with other agents such as the hypomethylating agents azacitidine or decitabine may provide a significant benefit to patients.

Hypomethylating agents, including azacitidine and decitabine, incorporate into DNA or RNA and inhibit the function of DNA methyltranferase enzymes. The loss of DNA methylation markers leads to cell death. Hypomethylating agents are used in older or unfit patients who cannot tolerate traditional chemotherapy and are an attractive treatment regimen backbone for combination with targeted agents due to their more favorable toxicity profile as compared to anthracyclines and cytarabine, the traditional chemotherapy combination used in AML (Dombret, Seymour et al. 2015). Clinical trials combining hypomethylating agents, especially azacitidine, with ivosidenib, enasidenib, and gemtuzumab-ozogamicin have shown promising results or are currently ongoing trials (DiNardo, Stein et al. 2018, Medeiros, Tanaka et al. 2018). The combination of azacitidine with crenolanib has shown some effect in vitro (Garz, Wolf et al. 2017). Hypomethylating agents provide one option for combination with one or more targeted agents and may allow for cytotoxic effects against any extant leukemic clones not expressing an actionable target.

Crenolanib is a novel, highly potent FLT3 inhibitor with activity against activating FLT3 mutations, such as FLT3-ITD, FLT3-TKD, or FLT3-variants, or those taught in U.S. Pat. Nos. 10,780,086, 10,463,658, 10,251,877, 10,213,423, 9,889,127, 9,801,870, 9,801,869, 9,480,683, 9,393,240, 9,101,624, or 9,023,880, or U.S. Application Publication No. 2019/0183880, relevant mutations incorporated herein by reference. Crenolanib has shown promising safety and response profiles in AML and solid tumors. It is ideally placed for use in combination regimens with BCL family protein inhibitors, MDM2 inhibitors, and/or p53 activators. Crenolanib is an orally bioavailable Tyrosine Kinase Inhibitor (TKI). It is significantly more selective for PDGFR, FLT3, and TRK kinases than other kinases, including c-KIT, VEGFR2, TIE2, FGFR2, EGFR, ERBB2, and SRC (Lewis, Lewis et al. 2009, Aikawa, Togashi et al. 2020). As a type 1 TKI that directly interacts with the ATP binding pocket, crenolanib binds to both the active and inactive conformations of the kinase. Importantly, crenolanib shows clinical activity against FLT3 and PDGFRA mutated proliferative disorders, and has a promising safety profile in both solid tumors and hematological malignancies (von Mehren, Tetzlaff et al. 2016, Goldberg 2020).

The present invention comprises methods of treating proliferative disorders in a subject. In one embodiment, the present invention provides a method for treating a proliferative disorder comprising the step of administering a compound of the present invention and a BCL protein inhibitor to the subject. In another embodiment, the present invention provides a method for treating a proliferative disorder comprising the step of administering a compound of the present invention and a MDM2 inhibitor to the subject. In another embodiment, the present invention provides a method for treating a proliferative disorder comprising the step of administering a compound of the present invention and a p53 stabilizer and/or activator to the subject.

Definitions

As used herein, the term "subject" refers to an animal, such as a mammal or a human, who has been the object of treatment, observation or experiment.

As used herein, the term "contacting" refers to the addition of crenolanib or a pharmaceutically available salt(s) thereof, to cells such that the compound is taken up by the cell.

As used herein, the term "therapeutically effective amount" refers to an amount of crenolanib or pharmaceutically acceptable salt(s) thereof, that elicits the biological or medicinal response in a subject that is being sought by a researcher, veterinarian, medical doctor or other clinician, which includes alleviation of the symptoms of the disease or the disorder being treated, reduction in the burden of the proliferative disorder (such as reduction in tumor size), and/or increase in progression-free or overall survival including prolonged stable disease. Methods for determining therapeutically effective doses for pharmaceutical compositions comprising a compound of the present invention are known in the art.

As used herein, the term "in combination with" refers to the administration of crenolanib or a pharmaceutically acceptable salt thereof and another targeted agent such as, for example, venetoclax, navitoclax, idasanutlin, or eprenetapopt, either concomitantly or sequentially in any order, such as, for example, at repeated intervals as during a standard course of treatment for a single cycle or more than one cycle such that one agent can be administered prior to, at the same time as, or subsequent to the administration of the other agents, such as, for example, azacitidine or decitabine, or any combination thereof.

As used herein, the term "composition" is intended to encompass a product comprising the specified combination of ingredients in the specified amounts, as well as any product which results, directly or indirectly, from combinations of the specified ingredients in the specified amounts.

As used herein, the term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. Examples of cell proliferative disorders are leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

As used herein, the term "relapsed/refractory" refers to a subject that was previously administered a pharmaceutical agent in order to treat a proliferative disease, but either did not respond to treatment (refractory), or progressed after initially responding (relapsed).

Detection of mutated FLT3 can be performed using any suitable means known in the art. For example, detection of gene mutations can be accomplished by detecting nucleic acid molecules (such as DNA) using nucleic acid amplification methods (such as RT-PCR) or high-throughput sequencing (i.e. "next-generation sequencing"). By example, next-generation sequencing platforms such as Illumina may be used to determine the exact genetic sequence of specific genes, or portions of genes, of interest. In brief, DNA from a tumor sample is fragmented, ligated with the appropriate primers and adaptors, and amplified using PCR during "library preparation". The prepared libraries are then sequenced using one of a number of commercially available systems which generates the sequence of the chosen target genes, all exomes, or the entire genome. The sequences are then analyzed using commercial available software, which aligns the tumor sample sequence to the known sequence of the genes of interest and performs a variant calling step, which identifies differences at the DNA level in the tumor sample and determines if such mutations would result in alteration of the amino acid sequence in the translated protein. Using these systems, a person of skill in the art can determine if a subject has one of the identified mutations with in FLT3. Further information on FLT3, including full gene and protein sequences, known clinically relevant variants and mutations, tissue expression, and signaling interaction partners can be found at UniProt (accession number P36888-1), GenBank (accession number NM_04119.2), and GenPept (accession number NP_004110.2).

FLT3 kinase inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon); Quizartinib (also known as AC220; Daiichi Sankyo); Gilteritinib (Asetllas). The following PCT International Applications and U.S. patent applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. Patent Application Publication No. 2004/0049032, relevant portions incorporated herein by reference. See also (Levis, Allebach et al. 2002, Yee, O'Farrell et al. 2002, Murata, Kumagai et al. 2003, O'Farrell, Abrams et al. 2003, Griswold, Shen et al. 2004, Levis and Small 2004, Smith, Levis et al. 2004, Stone, DeAngelo et al. 2005), relevant portions incorporated herein by reference.

The aforementioned inhibitors have either been, or are currently being, investigated in the preclinical setting, or phase I and II trials as monotherapy in relapsed AML, or in phase III combination studies in relapsed AML. Despite reports of successful inhibition of FLT3 with these compounds in preclinical studies, complete remissions have rarely been achieved in FLT3 mutant AML patients in the clinical setting. For the majority of patients, the clinical response is short-lived. Response criteria for AML clinical trials are adapted from the International Working Group for AML (Cheson, Bennett et al. 2003). Responders are patients who obtain a Complete Response (CR), Complete Response with incomplete blood count recovery (CRi), or Partial Remission (PR). Briefly, criteria are as follows:

1. Complete Remission (CR):
   a. Peripheral blood counts:
   i. No circulating blasts
   ii. Neutrophil count $\geq 1.0 \times 10^9/L$
   iii. Platelet count $\geq 100 \times 10^9/L$
   b. Bone marrow aspirate and biopsy:
   i. $\leq 5\%$ blasts
   ii. No Auer Rods
   iii. No extramedullary leukemia
2. Complete remission with incomplete blood count recovery (CRi):
   a. Peripheral blood counts:
   i. No circulating blasts
   ii. Neutrophil count $<1.0 \times 10^9/L$, or
   iii. Platelet count $<100 \times 10^9/L$
   b. Bone marrow aspirate and biopsy
   i. $\leq 5\%$ blasts
   ii. No Auer Rods
   iii. No extramedullary leukemia
3. Partial remission:
   a. All CR criteria if abnormal before treatment except:
   b. $\leq 50\%$ reduction in bone marrow blast but still $>5\%$ To date, clinical responses to FLT3 inhibitors have been primarily limited to clearance of peripheral blood (PB) blasts, which frequently return within a matter of weeks, while bone marrow (BM) blasts remain largely unaffected. For example, treatment with sorafenib, the prior mentioned multi-kinase inhibitor with activity against mutant FLT3, while effective in clearing PB blasts, has resulted in only modest BM blast reductions (Borthakur, Kantarjian et al. 2011). BM blast percentage plays a central role in the diagnosis and classification of AML. The presence of a heightened percentage of blasts in BM is associated with significantly shorter overall survival (Amin, Yang et al. 2005, Small 2006). To effectively treat FLT3 mutated AML patients and overcome the significant unmet need in this patient population, an inhibitor is required that significantly depletes both PB and BM blasts, bridges high risk and heavily pretreated patients to stem cell transplant, and can help to decrease relapse rates and increase overall survival in early stage disease patients.

In one embodiment, the present invention comprises therapeutically effective amounts of the compound having Formula I:

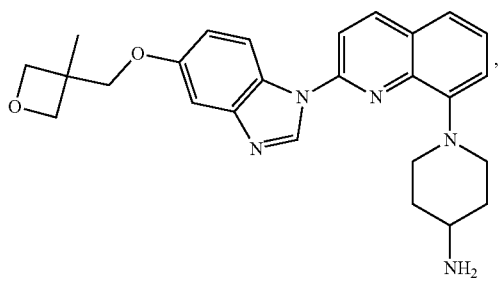 [SMILES: CC1(COc2ccc3c(c2)ncn3-c2ccc3cccc(N4CCC(N)CC4)c3n2)COC1]

or a pharmaceutically acceptable salt or solvate thereof, in combination with an BCL protein family inhibitor in a therapeutically effect amount against a proliferative disease that is selected from at least one of leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another embodiment, the present invention comprises therapeutically effective amounts of crenolanib or a pharmaceutically acceptable salt or solvate thereof, in combination with a MDM2 inhibitor against a proliferative disease. In another embodiment, the present invention comprises therapeutically effective amounts of crenolanib or a pharmaceutically acceptable salt or solvate thereof, in combination with a p53 activator and/or stabilizer against a proliferative disease.

Compounds of the present invention may be administered to a subject systemically, for example, orally, topically, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, the details of the disease condition. Factors associated with patient characteristics, such as age, weight, and diet will call for dosage adjustments. In other examples, the daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, the details of the disease condition. or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the Crenolanib of the present invention to a patient in need of therapy.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods, which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention.

Non-limiting examples of BCL protein family inhibitors which may be administered concomitantly or sequentially with crenolanib include venetoclax, navitoclax, palcitoclax, APG-2575, AT101, AZD0466, AZD4320, BCL201, BP1002, MIK665, 563845, VAL 101, AMG-176, AZD5991, FL118, AMG-397, ABBV-467 or ABT-737.

Non-limiting examples of MDM2 inhibitors which may be administered concomitantly or sequentially with crenolanib include idasanutlin, milademetan, siremadlin, AMG-232, ALRN-6924, APG-115, HQP1351, APG-2575, APG-1252 BI-907828, KRT-232, or CGM097.

Non-limiting examples of p53 activators and/or stabilizers which may be administered concomitantly or sequentially with crenolanib include eprenetapopt, APR-548, p-28, COTI-2, kevetrin, PC14586, or CV5461.

Non-limiting examples of hypomethylating agents or DNA methyltransferase inhibitors which may be administered concomitantly or sequentially with crenolanib include azacitidine, decitabine, guadecitabine, zebularine, RG108, EGCG, MG-98, SGI110, or SGI1027.

EXAMPLE 1

Effect of Crenolanib Besylate Combination Therapy with Azacitidine in a Relapsed/Refractory AML Patient with a FLT3-ITD Mutation: Remission and Bridge to Transplant.

Summary. Patient harbored a FLT-ITD at initial diagnosis of AML. After progressing on chemotherapy, the patient achieved remission on crenolanib besylate combination therapy with azacitidine and was bridged to transplant.

A 37-year-old male was initially diagnosed with AML. The patient was positive for a de novo FLT3-ITD mutation, categorizing him as a high-risk AML patient, which is associated with poor prognosis, increased cumulative risk of relapse, and shortened overall survival (Dohner, Estey et al. 2017).

The patient was initially treated with induction chemotherapy including a standard dose of cytarabine given as a continuous infusion for 7 days and 3 days of anthracycline delivered intravenously. Following one cycle of induction chemotherapy, the patient's bone marrow showed continued evidence of AML, and the patient was then administered a cycle of re-induction chemotherapy, in which the FLT3 inhibitor sorafenib was added to the standard cytarabine/anthracycline based regimen. Unfortunately, the patient's disease did not respond, and the patient was considered primary refractory. The patient was then administered a salvage chemotherapy regimen comprised of G-CSF, cytarabine, and clofarabine and achieved a complete remission (bone marrow blasts of ≤5%, recovery of both neutrophil and platelet counts). Approximately 2 months after achieving remission, a bone marrow biopsy showed that the patient had relapsed. Molecular testing revealed that the FLT3-ITD mutation present at diagnosis persisted.

To overcome the poor prognosis of the persistent FLT3-ITD mutation, the patient was provided oral crenolanib besylate in combination with intravenous azacitidine on a clinical trial for relapsed or refractory AML patients with activating FLT3 mutations (NCT02400281). At baseline, the patient presented with 64% bone marrow blasts. The patient began treatment with 75 mg/m$^2$/day of azacitidine for 7 days and 60 mg of oral crenolanib besylate three times daily for the remainder of the 28 days cycle. After 27 days of treatment, a bone marrow biopsy revealed that the patient had 3% bone marrow blasts, and the patient was confirmed to have achieved a CRi (complete remission with incomplete hematological recovery, the patient's neutrophils recovered, and platelets partially recovered). The patient was considered eligible for stem cell transplant and discontinued crenolanib treatment in order to receive such.

Crenolanib combination therapy with the hypomethylating agent azacitidine was able to achieve a complete remission in this patient with primary refractory AML who relapsed after achieving a remission to salvage chemotherapy.

EXAMPLE 2

Effect of Crenolanib Besylate Combination Therapy with Azacitidine in a Relapsed/Refractory AML Patient with a FLT3-ITD Mutation: Morphological Leukemia Free State.

Summary. Patient harbored a FLT-ITD mutation at initial diagnosis of AML. After progressing on chemotherapy, the patient achieved a morphological leukemia free state on crenolanib besylate combination therapy with azacitidine.

A 27 year old female was initially diagnosed with AML. The patient was positive for a de novo FLT3-ITD mutation, categorizing her as a high-risk AML patient, which is associated with poor prognosis, increased cumulative risk of relapse, and shortened overall survival (Dohner, Estey et al. 2017).

The patient was initially treated with induction chemotherapy including a standard dose of cytarabine given as a continuous infusion for 7 days and 3 days of anthracycline delivered intravenously. Following one cycle of induction chemotherapy, the patient's bone marrow showing continued evidence of AML, and the patient was then administered a cycle of re-induction chemotherapy, in which the FLT3 inhibitor sorafenib was added to the standard cytarabine/anthracycline based regimen. The patient achieved remission (bone marrow blasts of ≤5%, recovery of both neutrophil and platelet counts) and received a stem cell transplant followed by sorafenib maintenance therapy. Approximately 7 months after transplant, a bone marrow biopsy showed that the patient had relapsed. Molecular testing revealed that the FLT3-ITD mutation present at diagnosis persisted.

To overcome the poor prognosis of the persistent FLT3-ITD mutation, the patient was provided oral crenolanib besylate in combination with intravenous azacitidine on a clinical trial for relapsed or refractory AML patients with activating FLT3 mutations (NCT02400281). At baseline, the patient presented with 13% bone marrow blasts. The patient began treatment with 75 mg/m$^2$/day of azacitidine for 7 days and 80 mg of oral crenolanib besylate three times daily. After 28 days of treatment, a bone marrow biopsy revealed that the patient had 1% bone marrow blasts, and the patient was confirmed to have achieved a morphological leukemia free state (MLFS, ≤5% bone marrow blasts without neutrophil or platelet recovery). The patient continued single agent crenolanib besylate therapy for an additional 28 days and maintained a MLFS. Complications from the prior stem cell transplant, specifically liver graft-versus-host-disease, led the patient to choose to discontinue treatment.

Crenolanib combination therapy with azacitidine was able to achieve a morphological leukemia free state in this patient who relapsed within 1 year of transplant.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±0.1, 0.5, 1, 2, 3, 4, 5, 6, 7, 10, 12 or 15%, or as understood to be within a normal tolerance in the art, for example, within 2 standard deviations of the mean. Unless otherwise clear from the context, all numerical values provided herein are modified by the term about.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically, and by way of example, although the headings refer to a "Field of Invention," such claims should not be limited by the language under this heading to describe 30 the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Adams, J. M. and S. Cory (2018). "The BCL-2 arbiters of apoptosis and their growing role as cancer targets." Cell Death Differ 25(1): 27-36.

Aikawa, T., N. Togashi, K. Iwanaga, H. Okada, Y. Nishiya, S. Inoue, M. J. Levis and T. Isoyama (2020). "Quizartinib, a selective FLT3 inhibitor, maintains antileukemic activity in preclinical models of RAS-mediated midostaurin-resistant acute myeloid leukemia cells." Oncotarget 11(11).

Amin, H. M., Y. Yang, Y. Shen, E. H. Estey, F. J. Giles, S. A. Pierce, H. M. Kantarjian, S. M. O'Brien, I. Jilani and M. Albitar (2005). "Having a higher blast percentage in circulation than bone marrow: clinical implications in myelodysplastic syndrome and acute lymphoid and myeloid leukemias." Leukemia 19(9): 1567-1572.

Borthakur, G., H. Kantarjian, F. Ravandi, W. Zhang, M. Konopleva, J. J. Wright, S. Faderl, S. Verstovsek, S. Mathews, M. Andreeff and J. E. Cortes (2011). "Phase I study of sorafenib in patients with refractory or relapsed acute leukemias." Haematologica 96(1): 62-68.

Cheson, B. D., J. M. Bennett, K. J. Kopecky, T. Buchner, C. L. Willman, E. H. Estey, C. A. Schiffer, H. Doehner, M. S. Tallman, T. A. Lister, F. Lo-Coco, R. Willemze, A. Biondi, W. Hiddemann, R. A. Larson, B. Lowenberg, M. A. Sanz, D. R. Head, R. Ohno, C. D. Bloomfield, S. o. R. C. T. O. International Working Group for Diagnosis and L. Reporting Standards for Therapeutic Trials in Acute Myeloid (2003). "Revised recommendations of the International Working Group for Diagnosis, Standardization of Response Criteria, Treatment Outcomes, and Reporting Standards for Therapeutic Trials in Acute Myeloid Leukemia." J Clin Oncol 21(24): 4642-4649.

Chua, C. C., A. W. Roberts, J. Reynolds, C. Y. Fong, S. B. Ting, J. M. Salmon, S. MacRaild, A. Ivey, I. S. Tiong, S. Fleming, F. C. Brown, S. Loo, I. J. Majewski, S. K. Bohlander and A. H. Wei (2020). "Chemotherapy and Venetoclax in Elderly Acute Myeloid Leukemia Trial (CAVEAT): A Phase Ib Dose-Escalation Study of Venetoclax Combined With Modified Intensive Chemotherapy." Journal of Clinical Oncology 0(0): JCO.20.00572.

Chyla, B., N. Daver, K. Doyle, E. McKeegan, X. Huang, V. Ruvolo, Z. Wang, K. Chen, A. Souers, J. Leverson, J. Potluri, E. Boghaert, A. Bhathena, M. Konopleva and R. Popovic (2018). "Genetic Biomarkers Of Sensitivity and Resistance to Venetoclax Monotherapy in Patients With Relapsed Acute Myeloid Leukemia." Am J Hematol.

Dalle, I., H. Kontarjian, M. Ohanian, E. Jabbour, G. Garcia-Manero, K. Naqvi, W. Wierda, N. Daver, J. Burger, M. Konopleva, K. Takahashi, M. Andreef, N. Pemmaraju, A. Ferrajoli, G. Borthakur, T. Kadia, F. Ravandi and J. Cortes (2018). Phase I-II Study of Crenolanib Combined with Standard Salvage Chemotherapy and Crenolanib Combined with 5-Azacitidine in Acute Myeloid Leukemia Patients with FLT3 Activating Mutations. ASH.

DiNardo, C., A. Stein, E. M. Stein, A. Fathi, A. C. Schuh, P. Montesinos, O. Odenike, H. Kantarjian, R. Stone, R. Collins, G. Martinelli, M. Arnan, A. M. Zeidan, B. Wu, V. Zhang, J. VanOostendorp, J. Gong, K. J. Macbeth and P. Vyas (2018). Mutant-IDH Inhibitors, Ivosidenib or Enasidenib, in Combination with Azacitidine (AZA) in Patients with Newly Diagnosed Acute Myeloid Leukemia (AML) Ineligible for Chemotherapy. ASCO, Chicago, IL DiNardo, C. D., I. S. Tiong, A. Quaglieri, S. MacRaild, S. Loghavi, F. C. Brown, R. Thijssen, G. Pomilio, A. Ivey, J. Salmon, C. Glytsou, S. A. Fleming, Q. Zhang, H. Ma, K. P. Patel, S. M. Kornblau, Z. Xu, C. C. Chua, X. Chen, P. Blombery, C. Flensburg, N. Cummings, I. Aifantis, H. Kantarjian, D. C. S. Huang, Professor, A. W. Roberts, I. J. Majewski, M. Konopleva and A. H. Wei (2020). "Molecular patterns of response and treatment failure after frontline venetoclax combinations in older patients with AML." Blood.

Dohner, H., E. Estey, D. Grimwade, S. Amadori, F. R. Appelbaum, T. Buchner, H. Dombret, B. L. Ebert, P. Fenaux, R. A. Larson, R. L. Levine, F. Lo-Coco, T. Naoe, D. Niederwieser, G. J. Ossenkoppele, M. Sanz, J. Sierra, M. S. Tallman, H. F. Tien, A. H. Wei, B. Lowenberg and C. D. Bloomfield (2017). "Diagnosis and management of AML in adults: 2017 ELN recommendations from an international expert panel." Blood 129(4): 424-447.

Dombret, H., J. F. Seymour, A. Butrym, A. Wierzbowska, D. Selleslag, J. H. Jang, R. Kumar, J. Cavenagh, A. C. Schuh, A. Candoni, C. Recher, I. Sandhu, T. Bernal del Castillo, H. K. Al-Ali, G. Martinelli, J. Falantes, R. Noppeney, R. M. Stone, M. D. Minden, H. McIntyre, S. Songer, L. M. Lucy, C. L. Beach and H. Dohner (2015). "International phase 3 study of azacitidine vs conventional care regimens in older patients with newly diagnosed AML with >30% blasts." Blood 126(3): 291-299.

Frenzel, A., F. Grespi, W. Chmelewskij and A. Villunger (2009). "Bcl2 family proteins in carcinogenesis and the treatment of cancer." Apoptosis 14(4): 584-596.

Garz, A. K., S. Wolf, S. Grath, V. Gaidzik, S. Habringer, B. Vick, M. Rudelius, C. Ziegenhain, S. Herold, M. T. Weickert, M. Smets, C. Peschel, R. A. J. Oostendorp, S. Bultmann, I. Jeremias, C. Thiede, K. Dohner, U. Keller and K. S. Gotze (2017). "Azacitidine combined with the selective FLT3 kinase inhibitor crenolanib disrupts stromal protection and inhibits expansion of residual leukemia-initiating cells in FLT3-ITD AML with concurrent epigenetic mutations." Oncotarget 8(65): 108738-108759.

Goldberg, A. (2020). Younger Patients with Newly Diagnosed FLT3-Mutant AML Treated with Crenolanib Plus Chemotherapy Achieve Durable Remissions. EHA.

Griswold, I. J., L. J. Shen, P. La Rosee, S. Demehri, M. C. Heinrich, R. M. Braziel, L. McGreevey, A. D. Haley, N. Giese, B. J. Druker and M. W. Deininger (2004). "Effects of MLN518, a dual FLT3 and KIT inhibitor, on normal and malignant hematopoiesis." Blood 104(9): 2912-2918.

Joerger, A. C. and A. R. Fersht (2016). "The p53 Pathway: Origins, Inactivation in Cancer, and Emerging Therapeutic Approaches." Annu Rev Biochem 85: 375-404.

Konopleva, M., G. Martinelli, N. Daver, C. Papayannidis, A. Wei, B. Higgins, M. Ott, J. Mascarenhas and M. Andreeff (2020). "MDM2 inhibition: an important step forward in cancer therapy." Leukemia.

Konopleva, M., D. A. Pollyea, J. Potluri, B. Chyla, L. Hogdal, T. Busman, E. McKeegan, A. H. Salem, M. Zhu, J. L. Ricker, W. Blum, C. D. DiNardo, T. Kadia, M. Dunbar, R. Kirby, N. Falotico, J. Leverson, R. Humerickhouse, M. Mabry, R. Stone, H. Kantarjian and A. Letai (2016). "Efficacy and Biological Correlates of Response in a Phase II Study of Venetoclax Monotherapy in Patients with Acute Myelogenous Leukemia." Cancer Discov 6(10): 1106-1117.

Levis, M., J. Allebach, K. F. Tse, R. Zheng, B. R. Baldwin, B. D. Smith, S. Jones-Bolin, B. Ruggeri, C. Dionne and D. Small (2002). "A FLT3-targeted tyrosine kinase inhibitor is cytotoxic to leukemia cells in vitro and in vivo." Blood 99(11): 3885-3891.

Levis, M. and D. Small (2004). "Small molecule FLT3 tyrosine kinase inhibitors." Curr Pharm Des 10(11): 1183-1193.

Lewis, N. L., L. D. Lewis, J. P. Eder, N. J. Reddy, F. Guo, K. J. Pierce, A. J. Olszanski and R. B. Cohen (2009). "Phase I study of the safety, tolerability, and pharmacokinetics of oral CP-868,596, a highly specific platelet-derived growth factor receptor tyrosine kinase inhibitor in patients with advanced cancers." J Clin Oncol 27(31): 5262-5269.

Medeiros, B. C., T. N. Tanaka, L. Balaian, A. Bashey, A. Guzdar, H. Li, K. Messer and E. D. Ball (2018). "A Phase I/II Trial of the Combination of Azacitidine and Gemtuzumab Ozogamicin for Treatment of Relapsed Acute Myeloid Leukemia." Clin Lymphoma Myeloma Leuk 18(5): 346-352 e345.

Merino, D., G. L. Kelly, G. Lessene, A. H. Wei, A. W. Roberts and A. Strasser (2018). "BH3-Mimetic Drugs: Blazing the Trail for New Cancer Medicines." Cancer Cell 34(6): 879-891.

Murata, K., H. Kumagai, T. Kawashima, K. Tamitsu, M. Irie, H. Nakajima, S. Suzu, M. Shibuya, S. Kamihira, T. Nosaka, S. Asano and T. Kitamura (2003). "Selective cytotoxic mechanism of GTP-14564, a novel tyrosine kinase inhibitor in leukemia cells expressing a constitutively active Fms-like tyrosine kinase 3 (FLT3)." J Biol Chem 278(35): 32892-32898.

O'Farrell, A. M., T. J. Abrams, H. A. Yuen, T. J. Ngai, S. G. Louie, K. W. Yee, L. M. Wong, W. Hong, L. B. Lee, A. Town, B. D. Smolich, W. C. Manning, L. J. Murray, M. C. Heinrich and J. M. Cherrington (2003). "SU11248 is a novel FLT3 tyrosine kinase inhibitor with potent activity in vitro and in vivo." Blood 101(9): 3597-3605.

Small, D. (2006). "FLT3 mutations: biology and treatment." Hematology Am Soc Hematol Educ Program: 178-184.

Smith, B. D., M. Levis, M. Beran, F. Giles, H. Kantarjian, K. Berg, K. M. Murphy, T. Dauses, J. Allebach and D. Small (2004). "Single-agent CEP-701, a novel FLT3 inhibitor, shows biologic and clinical activity in patients with relapsed or refractory acute myeloid leukemia." Blood 103(10): 3669-3676.

Stone, R. M., D. J. DeAngelo, V. Klimek, I. Galinsky, E. Estey, S. D. Nimer, W. Grandin, D. Lebwohl, Y. Wang, P. Cohen, E. A. Fox, D. Neuberg, J. Clark, D. G. Gilliland and J. D. Griffin (2005). "Patients with acute myeloid leukemia and an activating mutation in FLT3 respond to a small-molecule FLT3 tyrosine kinase inhibitor, PKC412." Blood 105(1): 54-60.

von Mehren, M., E. D. Tetzlaff, M. Macaraeg, J. Davis, A. Vartika, R. Abhijit and M. C. Heinrich (2016). "Dose escalating study of crenolanib besylate in advanced GIST patients with PDGFRA D842V activating mutations." J Clin Oncol 34 (suppl; abstr 11010).

Yee, K. W., A. M. O'Farrell, B. D. Smolich, J. M. Cherrington, G. McMahon, C. L. Wait, L. S. McGreevey, D. J. Griffith and M. C. Heinrich (2002). "SU5416 and SU5614 inhibit kinase activity of wild-type and mutant FLT3 receptor tyrosine kinase." Blood 100(8): 2941-2949.

Yoshimoto, G., T. Miyamoto, S. Jabbarzadeh-Tabrizi, T. Iino, J. L. Rocnik, Y. Kikushige, Y. Mori, T. Shima, H. Iwasaki, K. Takenaka, K. Nagafuji, S. Mizuno, H. Niiro, G. D. Gilliland and K. Akashi (2009). "FLT3-ITD up-regulates MCL-1 to promote survival of stem cells in acute myeloid leukemia via FLT3-ITD-specific STAT5 activation." Blood 114(24): 5034-5043.

Zhang, Q., V. J. N. Bykov, K. G. Wiman and J. Zawacka-Pankau (2018). "APR-246 reactivates mutant p53 by targeting cysteines 124 and 277." Cell Death Dis 9(5): 439.

What is claimed is:

1. A method for treating a proliferative disorder comprising administering to a subject a therapeutically effective amount of crenolanib or pharmaceutically acceptable salt thereof in combination with a hypomethylating agent or DNA methyltransferase inhibitor.

2. The method of claim 1, wherein the hypomethylating agent is azacitidine or decitabine.

3. The method of claim 1, wherein the proliferative disorder is characterized by a constitutively active mutated FLT3, or wherein the mutated FLT3 is selected from at least one of FLT3-ITD, FLT3-TKD, or FLT3-variants.

4. The method of claim 1, wherein the proliferative disorder is selected from at least one of a leukemia, myeloma, myeloproliferative disease, myelodysplastic syndrome, idiopathic hypereosinophilic syndrome, bladder cancer, breast cancer, cervical cancer, central nervous system cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

5. The method of claim 1, wherein the subject has a newly diagnosed proliferative disorder.

6. The method of claim 1, wherein the crenolanib or pharmaceutically acceptable salt thereof and the hypomethylating agent or DNA methyltransferase inhibitor are administered one of sequentially or concomitantly with the hypomethylating agent or DNA methyltransferase inhibitor.

7. The method of claim 1, wherein the therapeutically effective amount of crenolanib or the pharmaceutically acceptable salt thereof is from about 50 to 500 mg per day, 100 to 450 mg per day, 200 to 400 mg per day, 300 to 500 mg per day, 350 to 500 mg per day, or 400 to 500 mg per day.

8. The method of claim 1, wherein the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate.

9. The method of claim 1, wherein the crenolanib or pharmaceutically acceptable salt thereof and the hypomethylating agent or DNA methyltransferase inhibitor are administered at least one of continuously, intermittently, systemically, or locally for as long as the subject is in need of treatment for the proliferative disorder.

10. The method of claim 1, wherein the crenolanib or pharmaceutically acceptable salt thereof and the hypomethylating agent or DNA methyltransferase inhibitor are administered orally, intravenously, or intraperitoneally.

11. The method of claim 1, wherein the crenolanib or pharmaceutically acceptable salt thereof and the hypomethylating agent or DNA methyltransferase inhibitor are administered up to three times a day.

12. The method of claim 1, wherein the subject has progressed on at least one prior line of therapy.

13. The method of claim 1, wherein the subject is in need of therapy to maintain remission.

* * * * *